United States Patent

Hoelderich et al.

Patent Number: 4,960,894
Date of Patent: Oct. 2, 1990

[54] PREPARATION OF SUBSTITUTED PYRIDINES

[75] Inventors: Wolfgang Hoelderich, Frankenthal; Norbert Goetz, Worms, both of Fed. Rep. of Germany

[73] Assignee: BASF Aktiengesellschaft, Ludwigshafen, Fed. Rep. of Germany

[21] Appl. No.: 278,362

[22] Filed: Dec. 1, 1988

[30] Foreign Application Priority Data

Dec. 4, 1987 [DE] Fed. Rep. of Germany ....... 3741160

[51] Int. Cl.$^5$ .................. C07D 213/09; C07D 213/12
[52] U.S. Cl. ................................ 546/250; 546/251; 546/290
[58] Field of Search ................................ 546/250, 251

[56] References Cited

U.S. PATENT DOCUMENTS

| | | | |
|---|---|---|---|
| 3,898,177 | 8/1975 | Beschke et al. | 502/203 |
| 3,917,542 | 11/1975 | Beschke et al. | 502/226 |
| 3,960,766 | 6/1976 | Beschke et al. | 502/208 |
| 4,163,854 | 8/1979 | Beschke et al. | 546/251 |
| 4,171,445 | 10/1979 | Beschke et al. | 546/251 |
| 4,220,783 | 9/1980 | Chang et al. | 546/251 |
| 4,675,410 | 6/1987 | Feitler et al. | 546/251 |
| 4,810,794 | 3/1989 | Shimizu et al. | 546/251 |

OTHER PUBLICATIONS

Orchin et al., The Vocabulary of Organic Chemistry, pp. 557–558, Wiley-Interscience Pub. (1980).

Primary Examiner—Alan L. Rotman
Attorney, Agent, or Firm—Keil & Weinkauf

[57] ABSTRACT

Preparation of substituted pyridines of the general formula (I)

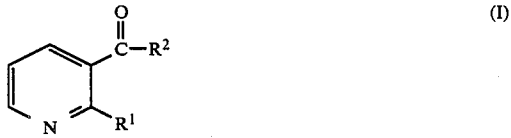

by the reaction of acrolein and ammonia with alkanals or ketones of the general formula (II), the acetals of the alkanals, $$R^2-CO-CH_2-CO-R^1 \qquad II$$

where $R^1$ is hydrogen or an alkyl of from 1 to 12 carbon atoms, cycloalkyl, aryl, or arylalkyl and $R^2$ is an alkyl or alkoxy radical; the reaction is carried out in the presence of zeolites.

7 Claims, No Drawings

PREPARATION OF SUBSTITUTED PYRIDINES

The present invention relates to a process for the preparation of substituted pyridines from acrolein, alkanals or ketones, and ammonia by catalyzed reaction in the presence of zeolite catalysts.

A review of the various methods of preparation for pyridine and substituted pyridines and the applications of such pyridine bases is found in Chem. Tech., 19(9), 528-37 (1967).

It is known that 3-methylpyridine is formed by the reaction of acrolein with ammonia in the gaseous phase in the presence of catalysts, particularly compounds of aluminum, fluorine, and oxygen that have been pretreated with oxygen at temperatures of from 550° C. to 1200° C. and also contain at least one other element from the second, third, or fourth group of the periodic system (DE-OS No. 21 51 417), or at least two elements of the second, fourth, fifth, or sixth group of the periodic system (DE-OS No. 22 24 160), or at least one element of subgroup 2A of the periodic system (DE-OS No. 22 39 801). Also known is a process in which acrolein and ammonia are fed separately into a fluidized bed and react therein (DE-OS No. 24 49 340). These processes have the disadvantage that considerable quantities of pyridine are also formed, the yield of 3-methylpyridine being less than 30%.

It is further known that 3-methylpyridine can be prepared by the reaction of mixtures of acrolein, propionaldehyde, and ammonia; aluminum oxide, silicon oxide, or mixtures of silicon oxide with from 5% to 50% of aluminum oxide, to which oxides of other elements may be added, are used as catalysts (FR-PS No. 1 273 826). In this process the yield of 3-methylpyridine is 53% at most.

According to DE-PS No. 2 703 070 the employment of very finely divided aluminum silicates with specific surfaces (BET) of from 200 m²/g to 800 m²/g raises yields of 3-methylpyridine from the levels of processes described above to up to 61%.

The preparation of pyridines substituted by aromatic and heteroaromatic radicals is known from DE-PS No. 2 819 196. Yields of phenylpyridine of up to 65% are obtained over compounds of aluminum, fluorine, and oxygen that have been pretreated at temperatures of from 550° C. to 1200° C. and also contain at least one other element from the second, third, or fourth group of the periodic system.

Even lanthanum-doped zeolitic molecular sieves are only moderately effective catalysts, giving low yields (DE-PS No. 2 023 158). Further disadvantages are that the reaction works only with acrolein and has to be carried out in the presence of oxygen (which presents safety hazards) and that a mixture is obtained (mole ratio 43% of pyridine to 22% of 3-methylpyridine).

A process for the preparation of pyridine and methylpyridine from ammonia and aldehydes of from 2 to 4 carbon atoms or ketones of from 3 to 5 carbon atoms over aluminosilicate zeolite ZSM 5 is described in U.S. Pat. No. 4,220,783. The reaction takes place in the presence of methanol or water; in the presence of formaldehyde more pyridine is formed. The catalyst is very soon deactivated: after 0.7 h the measured conversion is 93%, after 3 h only 78%. The yield—pyridine 7.7%, methylpyridine 59.6%—could also be better. In the presence of the other catalysts mentioned the yields are still worse, more hydrocarbons and products of high boiling point occurring.

It is known from EP No. 131 887 that when acid aluminosilicate zeolites of the pentasil type, with a constraint index of from 1 to 12, are used for the preparation of alkylpyridines they give better results in a fluidized bed than in a fixed bed (cf. U.S. Pat. No. 4,220,783). The highest total yield of pyridines from the reaction between acetaldehyde and formaldehyde is 89.8%, the ratio of pyridine to 3-methylpyridine being 2:1. The disadvantages of this process are that the catalyst has to be regenerated after a short time and that the product spectrum cannot be kept constant, even during short runs.

The industrial requirement was for a process by which pyridines substituted by functional groups could be synthesized selectively from readily accessible starting materials. It was further required that the catalysts employed for this purpose should excel by virtue of high activity and long life.

We have found that the disadvantages of the known processes are avoided and good yields are obtained from readily accessible starting materials when substituted pyridines of the general formula (I)

are prepared by the catalyzed reaction of acrolein and ammonia with alkanals or ketones of the general formula (II) or the acetals of the alkanals, $$R^2-CO-CH_2-CO-R^1 \quad \text{II}$$

where $R^1$ is hydrogen or an alkyl of from 1 to 12 carbon atoms, cycloalkyl, aryl, or arylalkyl and $R^2$ is an alkyl or alkoxy radical, if the reaction is carried out in the presence of zeolites.

The reaction is preferably carried out in the gaseous phase at a temperature of from 100° C. to 500° C.

The selective course of the synthesis from acrolein and bifunctional compounds in the presence of ammonia was surprising, since intermolecular reactions or secondary reactions between starting compounds and products could have been expected.

The starting materials apart from acrolein and ammonia are alkanals or ketones of the general formula (II), the acetals of the alkanals. Suitable compounds include acetylacetone, 4,4-dimethoxy-2-butanone, acetylacetaldehyde, methyl acetoacetate, propyl acetoacetate, esters of beta-keto acids, and propionylacetone.

The novel reaction can be illustrated by the following equation for the formation of 3-acetyl-2-methylpyridine:

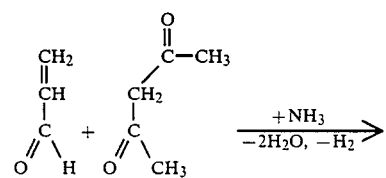

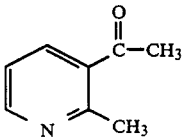

The catalysts used for the novel process are acid zeolites.

Zeolites are crystalline aluminosilicates with a highly ordered structure consisting of a rigid three-dimensional framework of $SiO_4$ and $AlO_4$ tetrahedra linked by common oxygen atoms. There is one silicon or aluminum atom to every two oxygen atoms—cf. Ullmanns Encyclopädie der technischen Chemie, 4th ed., vol. 24, p. 575 (1983). The electrovalency of the tetrahedra containing aluminum is balanced by inclusion of cations, such as alkali-metal or hydrogen cations, in the crystal. Cation exchange is possible. Before dehydration, by drying or calcination, the water molecules occupy interstices between the tetrahedra.

One or more elements other than aluminum—for instance gallium, iron, chromium, vanadium, arsenic, antimony, bismuth, or beryllium—can be built into the lattice. The silicon can also be replaced by tetravalent elements such as germanium, titanium, zirconium, or hafnium.

Zeolites are classified according to structure in various groups. Thus in the mordenite group the tetrahedra form chains, in the chabazite group sheets, and in the faujasite group polyhedra, for instance cubo-octahedra, made up of four-membered and six-membered rings. The cubo-octahedra can be linked in different ways to give voids and channels of various sizes, and zeolites of Types A, L, X, and Y are distinguished.

Catalysts suitable for the novel process are zeolites from the mordenite group, fine-pored zeolites from the erionite or chabazite group, or zeolites such as Type Y, X, or L zeolites from the faujasite group. The last group also includes so-called 'ultrastable' faujasitic zeolites; these are dealuminized zeolites, which can be prepared by processes described in: B. Imelik et al. (eds), Studies in Surface Science and Catalysis, vol. 5 (Catalysis by Zeolites), p. 203, Elsevier Scientific Publishing Co. (1980); Advances in Chemistry Series No. 101, Crystal Structures of Ultra-stable Faujasites, pp. 226 ff., American Chemical Society, Washington DC (1971); U.S. Pat. No. 4,512,961.

Zeolites of the pentasil type can be used to particular advantage. These are made up of five-membered rings of $SiO_4$ tetrahedra. They are characterized by high $SiO_2:Al_2O_3$ ratios and pore sizes intermediate between those of Type A and Type X or Y zeolites.

Such zeolites can have various chemical compositions: they may be aluminosilicates, borosilicates, ferrosilicates, beryllosilicates, gallosilicates, chromosilicates, arsenosilicates, antimonosilicates, bismuthosilicates, or mixtures of these, or they may be aluminogermanates, borogermanates, gallogermanates, ferrogermanates, or mixtures of these. Especially suitable are aluminosilicate, borosilicate, and ferrosilicate zeolites of the pentasil type.

The aluminosilicate zeolite can be synthesized from an aluminum compound, preferably aluminum hydroxide or aluminum sulfate, and a silicon compound, preferably finely divided silicon dioxide, in an aqueous solution of an amine, especially a polyamine such as 1,6-hexanediamine, 1,3-propanediamine, or triethylenetetramine, to which an alkali or akaline earth compound may be added if required, at a temperature of from 100° C. to 220° C. under autogenous pressure. Isotactic zeolites prepared as described in DE-OS No. 3 006 471 are also suitable. The aluminosilicate zeolites obtained contain $SiO_2$ and $Al_2O_3$ in mole ratios of from 10:1 to 40 000:1, depending on the relative amounts of the starting compounds. The synthesis of aluminosilicate zeolites can be carried out in an ether, such as di(ethylene glycol) dimethyl ether, an alcohol, such as methanol or 1,4-butanediol, or water.

The borosilicate zeolite can be synthesized at a temperature of from 90° C. to 200° C. under autogenous pressure from a boron compound, such as boric acid, and a silicon compound, preferably finely divided silicon dioxide, in an aqueous solution of an amine, especially 1,6-hexanediamine, 1,3-propanediamine, or triethylenetetramine, to which an alkali or alkaline earth compound may be added if required. The isotactic zeolites mentioned above (cf. DE-OS No. 3 006 471 and EP-PS No. 46 504) are however also suitable. The synthesis of such borosilicate zeolites can also be carried out in an ether, such as di(ethylene glycol) dimethyl ether, or an alcohol, such as or 1,6-hexanediol, instead of an aqueous solution of an amine.

The ferrosilicate zeolite can be synthesized from an iron compound, preferably ferric sulfate, and a silicon compound, preferably finely divided silicon dioxide, in an aqueous solution of an amine, especially 1,6-hexanediamine, to which an alkali or alkaline earth compound may be added if required, at a temperature of from 100° C. to 220° C. under autogenous pressure.

A number of other zeolites belong to the class of useful silicon-rich zeolites (containing $SiO_2$ and $Al_2O_3$ in a mole ratio of at least 10:1). These are: ZSM types, such as those described in U.S. Pat. No. 3,702,886 and elsewhere; ferrierite, a crystalline zeolite (EP-PS No. 12 473); NU-1, a crystalline zeolite described in U.S. Pat. No. 4,060,590; Silicalit ®, a molecular sieve described as a silica polymorph (U.S. Pat. No. 4,061,724).

After the synthetic zeolite (aluminosilicate, borosilicate, or ferrosilicate) has been isolated, dried at a temperature of from 100° C. to 160° C.—particularly 110 ° C.—, and calcined at from 450° C. to 550° C.—particularly 500° C.—it can be mixed with a binder in a mass ratio of from 90:10 to 40:60 and formed into extruded sticks or tablets. Suitable binders are various aluminium oxides, preferably boehmite, amorphous aluminosilicates containing $SiO_2$ and $Al_2O_3$ in a mole ratio of from 25:75 to 90:5, especially 75:25, silicon dioxide, preferably finely divided, mixtures of finely divided silicon dioxide, aluminum oxide, titanium dioxide, and zirconium dioxide, and clay. The extruded rods or pressed tablets are dried for 16 h at 110° C. and calcined for 16 h at 500° C.

Superior catalysts are also obtained if aluminosilicate or borosilicate zeolites are brought into the required form as soon as they have been isolated and dried, and only then calcined. Aluminosilicate and borosilicate zeolites can be employed as extruded sticks or tablets without any binder; it is Possible to use extrusion or peptizing aids, such as ethylcellulose, stearic acid, potato starch, formic, oxalic, acetic, or nitric acid, ammonia, amines, silicate esters, graphite, or mixtures of these.

If, because of the manner of their preparation, the zeolites are in a form other than the catalytically active acid form (H-form), for instance the Na-form, they can be completely or partially converted into the required H-form by ion-exchange with ammonium ions and subsequent calcination or by treatment with acids.

It is recommended that zeolite catalysts that have become deactivated by coking in the course of the novel process should be regenerated by burning off the carbon at a temperature of from 400° C. to 550° C., Particularly 500° C., in a current of air or air and nitrogen. In this way the zeolites recover their initial activity. Partial pre-coking can however be made use of to adjust the activity of the catalyst to a level corresponding to optimum selectivity for the required product of the reaction.

Modification of the zeolites is advantageous in order to attain the greatest possible selectivity, high conversion, and long catalyst life. An example of a suitable way of modifying zeolites is doping the zeolite powder or tablets etc. with metals, either by ion exchange or impregnation with metallic salts. The metals employed are: alkali metals, such as lithium, cesium, and potassium; magnesium; alkaline earth metals, such as calcium and strontium; metals of subgroups 3B, 4B, and 5B, such as aluminum, gallium, germanium, tin, lead, and bismuth; transition metals of groups 4 to 8, such as titanium, zirconium, vanadium, niobium, chromium, molybdenum, tungsten, manganese, rhenium, iron, ruthenium, osmium, cobalt, rhodium, iridium, nickel, palladium, and platinum; transition metals of groups 1 and 2, such as copper, silver, and zinc; rare-earth metals, such as lanthanum, cerium, praseodymium, neodymium, erbium, ytterbium, and lutetium.

A practical way of carrying out the doping is to pack a vertical tube with the pre-formed zeolite and pass through it an aqueous or ammoniacal solution of the nitrate or a halide of the one of the metals listed above at a temperature of from 20° C. to 100° C. Ion exchange can be carried out in this way with, for instance, the hydrogen, ammonium, or alkali form of the zeolite. Another way of applying the metal to the zeolite is to impregnate the material with an aqueous, ammoniacal, or alcoholic solution of a compound of one of the metals listed above, for instance a halide, nitrate, or oxide. Independent of whether ion exchange or impregnation is carried out, the catalyst must at least be dried afterwards; repeated calcination is optional.

A possible embodiment is, for example, to dissolve copper(II) nitrate trihydrate, nickel(II) nitrate hexahydrate, cerium(III) nitrate hexahydrate, lanthanum(II) nitrate hexahydrate, or cesium carbonate in water, soak the zeolite powder or tablets etc. in the solution for a certain time, say 30 min, and evaporate excess solution to dryness in a rotary evaporator. The impregnated zeolite is finally dried at a temperature of about 150° C. and calcined at about 550° C. This impregnation procedure can be repeated several times until the desired metal content is reached.

It is also possible to stir a slurry of pure zeolite powder in an aqueous solution of nickel nitrate or an ammoniacal solution of palladium nitrate for about 24 h at a temperature of from 40° C. to 100° C., then filter off the solid, dry it at about 150° C., and calcine it at about 500° C. The zeolitic material obtained in this way can be formed with or without binder into extruded sticks or pellets, or it can be used for fluidized beds.

One way of carrying out ion exchange on zeolites in the hydrogen, ammonium, or alkali form is to pack a column with sticks or pellets of the zeolite and circulate through it an aqueous solution of nickel nitrate or an ammoniacal solution of palladium nitrate for from 15 h to 20 h at a temperature between 30° C. and 80° C. The product is washed with water, dried at about 150° C., and calcined at about 550° C.

Aftertreatment with hydrogen is advantageous in the case of some metal-doped zeolites, for instance zeolites that have been doped with palladium, copper, or nickel.

Another possible way of modifying pre-formed or pulverulent zeolites is to treat them with acids—such as hydrochloric, hydrofluoric, or phosphoric acid—or steam, or both. A convenient method is to treat the zeolite powder with N phosphoric acid solution for 1 h at 80° C., then wash it with water, dry for 16 h at 100° C., and calcine for 20 h at 500° C. In another method the zeolite is treated before or after it has been mixed with binder and formed, for instance by warming it with aqueous hydrochloric acid solution in which the mass fraction of hydrogen chloride is from 3% to 25%—especially from 12% to 20%—for from 1 h to 3 h at temperatures of from 60° C. to 80° C.; the treated zeolite is finally washed with water, dried, and calcined at from 400° C. to 500° C.

A special method of acid treatment consists of boiling the zeolite powder under reflux with hydrofluoric acid solution of normality from 0.001N to 2N—especially from 0.05N to 0.5N—for from 0.5 h to 5 h—especially from 1 h to 3 h—; after the material has been filtered off and washed it is calcined, appropriately at temperatures of from 450° C. to 600° C. In another preferred method of acid treatment the pre-formed zeolite and binder is heated with aqueous hydrochloric acid solution in which the mass fraction of hydrogen chloride is from 12% to 20% for from 0.5 h to 5 h at temperatures of from 50° C. to 90° C.—especially from 60° C. to 80 ° C.—; the treated zeolite is finally washed, dried at from 100 ° C. to 160° C., and calcined at from 450° C. to 600° C. Treatment with hydrofluoric acid can follow treatment with hydrochloric acid.

Modification of zeolites can be carried out by the application of phosphorus compounds, such as trimethyl phosphate, trimethyl phosphite, and primary, secondary, or tertiary sodium phosphates. Treatment with primary sodium phosphate has proved particularly advantageous; it is carried out by soaking the zeolite sticks, tablets, or fluidizable powder in aqueous sodium dihydrogen phosphate solution, drying at 100° C., and calcining at 500° C.

The catalysts that have been described can be employed optionally as extruded sticks of diameter from 2 mm to 4 mm, tablets of diameter from 3 mm to 5 mm, coarse powder of particle size from 0.1 mm to 0.5 mm, or fluidizable powder.

The conditions of reaction for the novel process are chosen expediently from those that follow. The mole ratio of acrolein to alkanal (II) or ketone (III) to ammonia should be 1: between 1 & 2: between 1 & 15, preferably from 1:1:3 to 1:1:6. The reaction is best carried out in the gas phase, at a temperature of from 100° C. to 500° C.; it is advantageous to maintain the temperature at from 200° C. to 450° C., in particular from 250° C. to 400° C. Usually the reaction is carried out under a pressure of from 0.1 bar to 100 bar, especially from 0.5 bar to 10 bar.

When a gas-phase reaction between acrolein, an alkanal (II) or ketone (III), and ammonia is carried out over one of the catalysts described above, it is advantageous to keep to a catalyst load of from 0.1 $h^{-1}$ to 20 $h^{-1}$, especially from 1 h$^{-1}$ to 10 h$^{-1}$, where the catalyst load (WHSV) is the mass rate of flow of acrolein and alkanal or ketone per unit mass of catalyst.

The gas-phase reaction can be carried out in a fixed-bed or fluidized bed reactor.

It is also possible to carry out the reaction in the liquid phase at temperatures of from 20° C. to 200° C., with suspended catalyst or in a trickle-bed or flooded-bed reactor.

The reaction can be carried out batchwise or—preferably—continuously under atmospheric pressure, elevated pressure, or reduced Pressure. Non-volatile or solid starting compounds are introduced in solution, for instance dissolved in tetrahydrofuran, toluene, or light petroleum solvent. In general it is possible to dilute the starting compounds with solvents or inert gases, such as nitrogen, argon, or steam.

After the reaction the products can be isolated from the reaction mixture by the usual methods, for instance distillation. Unreacted starting compounds may be returned to the reaction.

The substituted pyridines prepared by means of the novel process are versatile intermediates.

EXAMPLES 1–8

The reaction was carried out in the gas phase under isothermal conditions for at least 6 h in a coiled tube reactor, internal diameter 0.6 cm, length 90 cm. The products of the reaction were separated and characterized by usual methods; they and the starting compounds were determined quantitatively by known gas-chromatographic methods.

The catalysts employed in the novel process were as follows.

Catalyst A

Borosilicate zeolite of the pentasil type was prepared by hydrothermal synthesis in a stirred autoclave at a temperature of 170° C. under autogenous pressure from 640 g of finely divided silicon dioxide and 122 g of boric acid in 8000 g of a mixture consisting of equal parts by weight of 1,6-hexanediamine and water. The crystalline product was filtered off, washed, dried for 24 h at 100° C., and calcined for 24 h at 500° C. The mass fractions of SiO$_2$ and B$_2$O$_3$ in the borosilicate zeolite were 94.2% and 2.3%.

A mixture of this zeolite with boehmite in the mass ratio of 60:40 was extruded into 2-mm sticks, which were dried for 16 h at 110° C. and calcined for 24 h at 500° C.

Catalyst B

Aluminosilicate zeolite of the pentasil type was prepared under hydrothermal conditions in a stirred autoclave at a temperature of 150° C. under autogenous pressure from 65 g of finely divided silicon dioxide and 20.3 g of aluminum sulfate octadecahydrate in 1000 g of a mixture consisting of equal parts by weight of 1,6-hexanediamine and water. The crystalline product was filtered off, washed, dried for 24 h at 100° C., and calcined for 24 h at 500° C. The mass fractions of SiO$_2$ and Al$_2$O$_3$ in the aluminosilicate zeolite were 91.6% and 4.6%.

A mixture of this zeolite with boehmite in the mass ratio of 60:40 was extruded into 2-mm sticks, which were dried for 16 h at 110° C. and calcined for 24 h at 500° C.

Catalyst C

Some of the borosilicate zeolite obtained as Catalyst A (100 g) was treated with 280 ml of 0.1N hydrofluoric acid solution for 2 h at 90° C., then filtered off and dried at 160° C.

A mixture of this zeolite with amorphous aluminosilicate (75% SiO$_2$ and 25% Al$_2$O$_3$ by weight) in the mass ratio of 60:40 was extruded into 2-mm sticks, which were dried for 16 h at 110° C. and calcined for 24 h at 500° C.

Catalyst D

A mixture of commercial Type Y sodium zeolite with boehmite in the mass ratio of 60:40 was extruded into 2-mm sticks, which were dried for 16 h at 110° C. and calcined for 24 h at 540° C.

The sticks were subjected to ion exchange in a 20% aqueous solution of lanthanum nitrate for 2 h at 80° C., then dried at 100° C. and calcined at 500° C. At this stage the mass fractions of lanthanum and sodium should have been 7.1% and 1.1%; if necessary ion exchange followed by calcination was repeated until these values were reached.

Catalyst E

Some of Catalyst A was impregnated with aqueous cerium(III) nitrate solution, dried for 2 h at 130° C., and calcined for 2 h at 540° C. The mass fraction of cerium in the product was 2.5%.

Details of the experimental conditions for Examples 1–6 and the results obtained are given in Table 1.

TABLE 1

Preparation of 3-acetyl-2-methylpyridine from acrolein, acetylacetone, and ammonia (mole ratio 1:1:3); catalyst load (WHSV) 3.0 h$^{-1}$

| Example | 1 | 2 | 3 | 4 | 5 | 6 |
|---|---|---|---|---|---|---|
| Catalyst | A | B | C | D | D | E |
| t/°C. | 350 | 350 | 350 | 350 | 300 | 350 |
| Conversion$^a$/% | 100 | 100 | 100 | 100 | 100 | 100 |
| Selectivity$^b$/% | 79.0 | 58.2 | 66.5 | 64.9 | 72.7 | 64.0 |

$^a$Conversion of both acrolein and acetylacetone.
$^b$For 3-acetyl-2-methylpyridine; other products were pyridine, 2-methylpyridine, 3-methylpyridine, acetamide, acetonitrile, dimethylpyridines, and 4-amino-3-penten-2-one.

EXAMPLE 7

Acrolein, 4,4-dimethoxy-2-butanone, and ammonia in the mole ratio 1:1:6 reacted at 350 ° C. over Catalyst C in the reactor described above; the catalyst load (WHSV) was 1.5 h$^{-1}$.

Conversion of acrolein was 100%. The main products were methanol and 3-acetylpyridine. Acetone, acetonitrile, pyridine, and methylpyridines were also formed. Selectivity for 3-acetylpyridine was 52.4%; when the catalyst load was 3 h$^{-1}$ the selectivity was 56.9%.

EXAMPLE 8

Acrolein, methyl acetoacetate, and ammonia in the mole ratio 1:1:3 reacted at 350° C. over Catalyst C in the reactor described above; the catalyst load (WHSV) was 2.5 h$^{-1}$.

Conversion of both acrolein and methyl acetoacetate was 100%. Selectivity for methyl 2-methyl-3-pyridinecarboxylate was 45.7%. Other products included 3-cyano-2-methylpyridine, 2-methyl-3- pyridinecarboxamide, 2-methylpyridine, and 3-methylpyridine.

We claim:

1. A process for the preparation of substituted pyridines of the formula (I),

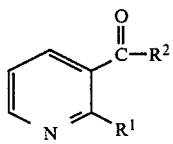

wherein $R^1$ is hydrogen or $C_1$–$C_{12}$-alkyl and $R^2$ is methyl, ethyl or $C_1$–$C_3$-alkoxy, which comprises: reacting acrolein and ammonia with a dicarbonyl compound of the formula (II),

or, if $R^1$ is hydrogen, optionally with an acetal of the compound of formula (II), in the presence of an acidic zeolite catalyst and either in the gas phase at a temperature of 100° C. to 500° C. or in the liquid phase at a temperature of 20° C. to 200° C.

2. The process of claim 1 wherein the compound of formula (II) is acetylacetone, 4,4-dimethoxy-2-butanone (3-oxobutyraldehyde dimethyl acetal), or methyl acetoacetate.

3. The process of claim 1 wherein the catalyst is a zeolite of the pentasil type.

4. The process of claim 1 wherein the catalyst is a borosilicate, ferrosilicate, or aluminosilicate zeolite of the pentasil type.

5. The process of claim 1 wherein the catalyst is an aluminosilicate zeolite of the faujasite group.

6. The process of claim 1 wherein the catalyst is a zeolite doped with an alkali, alkaline-earth, transition, or rare-earth metal.

7. The process of claim 1 wherein the reaction is carried out in the gaseous phase.

* * * * *